US008586780B2

(12) United States Patent
Hagemeyer et al.

(10) Patent No.: US 8,586,780 B2
(45) Date of Patent: Nov. 19, 2013

(54) DOPED PD/AU SHELL CATALYST, METHOD FOR PRODUCING THE SAME AND USE THEREOF

(75) Inventors: Alfred Hagemeyer, Bad Aibling (DE); Gerhard Mestl, München (DE); Peter Scheck, Gilching (DE)

(73) Assignee: Sued-Chemie IP GmbH & Co. KG, Munich (DE)

( * ) Notice: Subject to any disclaimer, the term of this patent is extended or adjusted under 35 U.S.C. 154(b) by 23 days.

(21) Appl. No.: 12/601,419

(22) PCT Filed: May 30, 2008

(86) PCT No.: PCT/EP2008/004336
§ 371 (c)(1),
(2), (4) Date: May 17, 2010

(87) PCT Pub. No.: WO2008/145395
PCT Pub. Date: Dec. 4, 2008

(65) Prior Publication Data
US 2010/0273644 A1   Oct. 28, 2010

(30) Foreign Application Priority Data

May 31, 2007 (DE) .......................... 10 2007 025 362

(51) Int. Cl.
*C07C 67/04* (2006.01)
*B01J 23/00* (2006.01)
*B01J 21/00* (2006.01)

(52) U.S. Cl.
USPC ................. 560/247; 502/65; 502/66; 502/73; 502/74; 502/87; 502/243; 502/245; 502/262; 502/263; 502/302; 502/303; 502/304; 502/327; 502/330; 502/332; 502/333; 502/339; 502/344; 502/349; 502/350; 502/351; 502/355; 502/415; 502/439

(58) Field of Classification Search
USPC ........... 502/65, 66, 73, 74, 87, 243, 245, 262, 502/263, 302, 303, 304, 327, 330, 332, 333, 502/339, 344, 349, 350, 351, 355, 415, 502/439; 560/247
See application file for complete search history.

(56) References Cited

U.S. PATENT DOCUMENTS

| | | | |
|---|---|---|---|
| 2,656,323 A | 10/1953 | Bielawski et al. | |
| 3,252,757 A | 5/1966 | Granquist | |
| 3,259,589 A | 7/1966 | Michalko | |
| 3,565,919 A | 2/1971 | Friedrichsen et al. | |
| 3,617,489 A | 11/1971 | Csicsery | |
| 4,155,730 A | 5/1979 | Biberbach et al. | |
| 4,407,733 A | 10/1983 | Birkenstock et al. | |
| 4,409,410 A | 10/1983 | Cosyns et al. | |
| 4,521,618 A | 6/1985 | Arntz et al. | |
| 4,621,072 A | 11/1986 | Arntz et al. | |
| 4,844,790 A | 7/1989 | Occelli | |
| 4,970,804 A | 11/1990 | Hüttlin | |
| 4,977,126 A | 12/1990 | Mauldin et al. | |
| 4,990,266 A | 2/1991 | Vorlop et al. | |
| 5,015,453 A | 5/1991 | Chapman | |
| 5,066,365 A | 11/1991 | Roscher et al. | |
| 5,145,650 A | 9/1992 | Hüttlin | |
| 5,175,136 A * | 12/1992 | Felthouse | 502/242 |
| 5,179,056 A | 1/1993 | Bartley | |
| 5,189,123 A * | 2/1993 | Gropper et al. | 526/106 |
| 5,213,771 A | 5/1993 | Hilliard et al. | |
| 5,250,487 A * | 10/1993 | Wirtz et al. | 502/243 |
| 5,304,525 A | 4/1994 | Immel et al. | |
| 5,422,329 A | 6/1995 | Wirtz et al. | |
| 5,559,071 A | 9/1996 | Abel et al. | |
| 5,567,839 A | 10/1996 | Gulliver et al. | |
| 5,571,771 A | 11/1996 | Abel et al. | |
| 5,591,688 A | 1/1997 | Blum et al. | |
| 5,622,908 A | 4/1997 | Abel et al. | |
| 5,648,576 A | 7/1997 | Nguyen Than et al. | |
| 5,650,371 A | 7/1997 | Culross | |
| 5,665,667 A | 9/1997 | Lemanski et al. | |
| 5,668,074 A | 9/1997 | Wu et al. | |
| 5,700,753 A | 12/1997 | Wang et al. | |
| 5,753,583 A | 5/1998 | Heineke et al. | |

(Continued)

FOREIGN PATENT DOCUMENTS

| | | |
|---|---|---|
| CA | 1267880 | 4/1990 |
| CA | 1267882 | 4/1990 |

(Continued)

OTHER PUBLICATIONS

Elliott P. Barrett et al., "The Determination of Pore Volume and Area Distributions in Porous Substances. I. Computations from Nitrogen Isotherms," *J. Am. Chem. Soc.*, vol. 73, 1951, pp. 373-380.

(Continued)

*Primary Examiner* — Cam N. Nguyen
(74) *Attorney, Agent, or Firm* — RatnerPrestia

(57) ABSTRACT

A shell catalyst for producing vinyl acetate monomer (VAM), comprising an oxidic porous catalyst support, formed as a shaped body, with an outer shell in which metallic Pd and Au are contained. To provide a shell catalyst for producing VAM which has a relatively high activity and can be obtained at relatively low cost, the catalyst support is doped with at least one oxide of an element selected from the group consisting of Li, P, Ca, V, Cr, Mn, Fe, Sr, Nb, Ta, W, La and the rare-earth metals.

47 Claims, No Drawings

(56) References Cited

U.S. PATENT DOCUMENTS

| | | | |
|---|---|---|---|
| 5,801,285 A | 9/1998 | Waldmann et al. | |
| 5,808,136 A | 9/1998 | Tacke et al. | |
| 5,888,472 A | 3/1999 | Bem et al. | |
| 5,935,889 A | 8/1999 | Murrell et al. | |
| 5,990,344 A | 11/1999 | Couves et al. | |
| 6,015,769 A | 1/2000 | Wang | |
| 6,017,847 A | 1/2000 | Wang | |
| 6,074,979 A | 6/2000 | Hagemeyer et al. | |
| 6,090,746 A | 7/2000 | Bönnemann et al. | |
| 6,156,927 A | 12/2000 | Halcom et al. | |
| 6,207,610 B1 * | 3/2001 | Krause et al. | 502/232 |
| 6,228,800 B1 * | 5/2001 | Yamaguchi et al. | 502/339 |
| 6,268,522 B1 | 7/2001 | Hagemeyer et al. | |
| 6,288,295 B1 | 9/2001 | Didillon et al. | |
| 6,313,063 B1 | 11/2001 | Rytter et al. | |
| 6,316,383 B1 | 11/2001 | Tacke et al. | |
| 6,350,717 B1 * | 2/2002 | Frenzel et al. | 502/330 |
| 6,350,900 B1 | 2/2002 | Wang et al. | |
| 6,358,882 B1 | 3/2002 | Salem et al. | |
| 6,367,165 B1 | 4/2002 | Hüttlin | |
| 6,395,676 B2 | 5/2002 | Blum et al. | |
| 6,399,813 B1 | 6/2002 | Blum et al. | |
| 6,420,308 B1 * | 7/2002 | Khanmamedova | 502/344 |
| 6,486,093 B2 | 11/2002 | Wang et al. | |
| 6,492,299 B1 | 12/2002 | Couves et al. | |
| 6,528,453 B2 | 3/2003 | Baker et al. | |
| 6,528,683 B1 | 3/2003 | Heidemann et al. | |
| 6,534,438 B1 | 3/2003 | Baker et al. | |
| 6,534,672 B2 | 3/2003 | Salem et al. | |
| 6,593,270 B1 | 7/2003 | Krause et al. | |
| 6,603,038 B1 * | 8/2003 | Hagemeyer et al. | 560/241.1 |
| 6,605,739 B1 | 8/2003 | Karim et al. | |
| 6,734,131 B2 * | 5/2004 | Shih et al. | 502/80 |
| 6,797,669 B2 * | 9/2004 | Zhang et al. | 502/339 |
| 6,806,382 B2 | 10/2004 | Baker et al. | |
| 6,821,922 B1 | 11/2004 | Tacke et al. | |
| 6,849,243 B1 | 2/2005 | Hagemeyer et al. | |
| 6,898,869 B2 | 5/2005 | Hüttlin | |
| 6,949,141 B2 | 9/2005 | Hüttlin | |
| 6,987,200 B2 | 1/2006 | Hagemeyer et al. | |
| 6,992,040 B2 * | 1/2006 | Muller et al. | 502/327 |
| 7,288,686 B2 * | 10/2007 | Ryu | 585/259 |
| 7,468,455 B2 | 12/2008 | Mazanec et al. | |
| 7,569,508 B2 | 8/2009 | Zhou et al. | |
| 7,797,854 B2 | 9/2010 | Huettlin | |
| 8,207,327 B2 | 6/2012 | Laar et al. | |
| 2001/0018401 A1 | 8/2001 | Blum et al. | |
| 2001/0048970 A1 | 12/2001 | Hagemeyer et al. | |
| 2002/0028966 A1 | 3/2002 | Blum et al. | |
| 2002/0052290 A1 * | 5/2002 | Bowman et al. | 502/243 |
| 2002/0062039 A1 | 5/2002 | Salem et al. | |
| 2003/0036476 A1 | 2/2003 | Arnold et al. | |
| 2003/0144544 A1 | 7/2003 | Baker et al. | |
| 2003/0187293 A1 | 10/2003 | Birke et al. | |
| 2003/0187294 A1 | 10/2003 | Hagemeyer et al. | |
| 2003/0195114 A1 | 10/2003 | Tacke et al. | |
| 2003/0233012 A1 | 12/2003 | Jackson et al. | |
| 2004/0048937 A1 | 3/2004 | Srinivasan et al. | |
| 2004/0235650 A1 | 11/2004 | Saleh et al. | |
| 2005/0034322 A1 | 2/2005 | Hüttlin | |
| 2005/0181940 A1 | 8/2005 | Wang et al. | |
| 2005/0203320 A1 * | 9/2005 | Ryu | 585/261 |
| 2006/0135809 A1 | 6/2006 | Kimmich et al. | |
| 2006/0266673 A1 | 11/2006 | Rende et al. | |
| 2007/0041795 A1 | 2/2007 | Neto et al. | |
| 2007/0135302 A1 | 6/2007 | Neto et al. | |
| 2007/0191651 A1 | 8/2007 | Coupard et al. | |
| 2007/0234586 A1 | 10/2007 | Huettlin | |
| 2008/0287290 A1 | 11/2008 | Wang et al. | |
| 2010/0140181 A1 | 6/2010 | Tastayre | |
| 2011/0166010 A1 | 7/2011 | Hagemeyer et al. | |

FOREIGN PATENT DOCUMENTS

| | | |
|---|---|---|
| CA | 1268018 | 4/1990 |
| CA | 1268165 | 4/1990 |
| CA | 2 338 961 A1 | 2/2000 |
| DE | 1 286 021 B1 | 1/1969 |
| DE | 27 03 801 A1 | 8/1978 |
| DE | 28 48 978 A1 | 5/1980 |
| DE | 29 45 913 A1 | 6/1981 |
| DE | 31 19 850 A1 | 2/1982 |
| DE | 261 104 A5 | 10/1988 |
| DE | 40 06 935 A1 | 9/1991 |
| DE | 40 39 026 A1 | 6/1992 |
| DE | 44 05 876 A1 | 10/1995 |
| DE | 44 43 705 A1 | 6/1996 |
| DE | 195 34 493 A1 | 3/1997 |
| DE | 195 38 799 A1 | 4/1997 |
| DE | 196 01 861 A1 | 7/1997 |
| DE | 197 34 974 A1 | 2/1999 |
| DE | 197 34 975 A1 | 3/1999 |
| DE | 198 34 569 A1 | 2/2000 |
| DE | 199 04 147 A1 | 8/2000 |
| DE | 199 14 066 A1 | 10/2000 |
| DE | 100 64 084 A1 | 7/2002 |
| DE | 697 11 320 T2 | 7/2002 |
| DE | 102 48 116 B3 | 4/2004 |
| DE | 602 06 752 T2 | 7/2006 |
| DE | 20 2005 003 791 U1 | 8/2006 |
| DE | 10 2005 029 200 A1 | 12/2006 |
| EP | 0 064 301 A1 | 11/1982 |
| EP | 0 370 167 A1 | 5/1990 |
| EP | 0 436 787 A2 | 7/1991 |
| EP | 0 565 952 A1 | 10/1993 |
| EP | 0 634 208 A1 | 1/1995 |
| EP | 0 634 209 A1 | 1/1995 |
| EP | 0 634 214 A1 | 1/1995 |
| EP | 0 723 810 | 7/1996 |
| EP | 0 839 793 A1 | 5/1998 |
| EP | 0 839 797 A1 | 5/1998 |
| EP | 0 882 507 A1 | 12/1998 |
| EP | 0 899 013 A1 | 3/1999 |
| EP | 1 102 635 | 2/2000 |
| EP | 1 323 469 A2 | 7/2003 |
| EP | 1 452 230 A1 | 9/2004 |
| EP | 1 979 073 | 7/2007 |
| GB | 1 258 371 | 1/1970 |
| GB | 1 229 749 | 4/1971 |
| GB | 1 283 737 | 8/1972 |
| JP | 2003-527962 | 9/2003 |
| JP | 2006-239588 | 9/2006 |
| JP | 2006-255600 | 9/2006 |
| JP | 2007-506540 | 3/2007 |
| WO | WO 98/14274 | 4/1998 |
| WO | WO 98/18553 | 5/1998 |
| WO | WO 98/18553 A1 | 5/1998 |
| WO | WO 98/37102 | 8/1998 |
| WO | WO 99/22860 | 5/1999 |
| WO | WO 99/62632 | 12/1999 |
| WO | WO 00/58008 | 10/2000 |
| WO | WO 00/58008 A1 | 10/2000 |
| WO | WO 02/100527 A1 | 12/2002 |
| WO | WO 2005/061107 A1 | 7/2005 |
| WO | WO 2005/065821 A1 | 7/2005 |
| WO | WO 2006/027009 A1 | 3/2006 |
| WO | WO 2006/045606 A1 | 5/2006 |
| WO | WO 2008/107050 A1 | 9/2008 |

OTHER PUBLICATIONS

Stephen Brunauer et al., "Adsorption of Gases in Multimolecular Layers," *J. Am. Chem. Soc.*, vol. 60, 1938, pp. 309-319.

Textbook of Inorganic Chemistry, Hollemann Wiberg, de Gruyter, $102^{nd}$ Edition, 2007 (ISBN 978-3-11-017770-1), at pp. 955-959, 965-970.

Römpp Chemical Dictionary, $10^{th}$ Edition, Georg Thieme Verlag, at pp. 374-375.

Römpp Chemical Dictionary, $10^{th}$ Edition, Georg Thieme Verlag, at pp. 3427-3428.

(56) References Cited

OTHER PUBLICATIONS

Römpp Chemical Dictionary, 10*th* Edition (1997), Georg Thieme Verlag, at pp. 374-375.
Römpp Chemical Dictionary, 10*th* Edition (1997), Georg Thieme Verlag, at pp. 3427-3428.
L.A. Boot et al., Characterization of pre-shaped zirconia bodies for catalytic applications, Journal of Material Science, vol. 31, 1996, pp. 3115-3121.
Kohl et al., Gas purification, 5*th* Edition, Gulf Publishing Company pp. 40-73 (1997).
Komai et al., Journal of Catalysis 120, 370-376 (1989).
Lehrbuch de anorganischen Chemie, Hollemann Wiberg, de Gruyter 102, Auflage, (ISBN 978-3-11-017770-1), pp. 955-970, term Schichtsllkate (2007).
Reddy et al., Fluor's Econamine FG Plus*SM* Technology, presented at the Second National Conference on Carbon Sequestration, National Energy Technology Department of Energy, Alexandria, VA, USE, pp. 1-11, May 5-8, 2003.
Usubharatana et al., Energy Procedia, vol. 1, Issue 1, pp. 95-102 (2009).
Office Action in U.S. Appl. No. 12/601,399 dated May 9, 2012.
Response filed in U.S. Appl. No. 12/601,399 on Aug. 9, 2012.
Office Action in U.S. Appl. No. 12/601,420 dated Aug. 6, 2012.
Response filed in U.S. Appl. No. 12/601,420 on Oct. 18, 2012.
Office Action in U.S. Appl. No. 12/601,777 dated Jan. 9, 2012.
Response filed in U.S. Appl. No. 12/601,777 on May 9, 2012.
Office Action in U.S. Appl. No. 12/601,777 dated Jun. 12, 2012.
Response filed in U.S. Appl. No. 12/601,777 on Sep. 12, 2012.
Office Action in U.S. Appl. No. 12/602,315 dated Aug. 16, 2012.
Office Action in U.S. Appl. No. 12/601,900 dated Jan. 4, 2012.
Office Action in U.S. Appl. No. 12/601,985 dated Feb. 7, 2013.
Montmorillonite, Mineral Data Publishing, Version 1.2 (2001).

\* cited by examiner

DOPED PD/AU SHELL CATALYST, METHOD FOR PRODUCING THE SAME AND USE THEREOF

CROSS REFERENCE TO RELATED APPLICATIONS

This is a National Phase application of PCT application number PCT/EP2008/004336, filed May 30, 2008, which claims priority benefit of German application number DE 10 2007 025 362.3, filed May 31, 2007, the content of such applications being incorporated herein by reference.

FIELD OF THE INVENTION

The present invention relates to a shell catalyst for producing vinyl acetate monomer (VAM), comprising an oxidic porous catalyst support, formed as a shaped body, with an outer shell in which metallic Pd and Au are contained.

BACKGROUND OF THE INVENTION

VAM is an important monomer building block in the synthesis of plastic polymers. The main fields of use of VAM are i.a. the production of polyvinyl acetate, polyvinyl alcohol and polyvinyl acetal and also co- and terpolymerization with other monomers such as for example ethylene, vinyl chloride, acrylate, maleinate, fumarate and vinyl laurate.

VAM is produced predominantly in the gas phase from acetic acid and ethylene by reaction with oxygen, wherein the catalysts used for this synthesis preferably contain Pd and Au as active metals and also an alkali metal component as promoter, preferably potassium in the form of the acetate. In the Pd/Au system of these catalysts, the active metals Pd and Au are probably not present in the form of metal particles of the respective pure metal, but rather in the form of Pd/Au-alloy particles of possibly different composition, although the presence of unalloyed particles cannot be ruled out. As an alternative to Au, for example Cd or Ba can also be used as second active metal component.

Currently, VAM is predominantly produced by means of so-called shell catalysts in which the catalytic active metals of the catalyst do not fully penetrate the catalyst support formed as a shaped body, but rather are contained only in an outer area (shell) of greater or lesser width of the catalyst support shaped body (cf. on this EP 565 952 A1, EP 634 214 A1, EP 634 209 A1 and EP 634 208 A1), while the areas of the support lying further inside are almost free of active metals. With the help of shell catalysts, a more selective reaction control is possible in many cases than with catalysts in which the supports are impregnated into the core of the support with the active components ("impregnated through").

The shell catalysts known in the state of the art for producing VAM can be for example catalyst supports based on silicon oxide, aluminium oxide, aluminosilicate, titanium oxide or zirconium oxide (cf. on this EP 839 793 A1, WO 1998/018553 A1, WO 2000/058008 A1 and WO 2005/061107 A1). Catalyst supports based on titanium oxide or zirconium oxide are currently scarcely used, however, since these catalyst supports display no long-term resistance to acetic acid and are relatively expensive.

DESCRIPTION OF THE INVENTION

The great majority of the catalysts currently used for producing VAM are shell catalysts with a Pd/Au shell on an oxidic porous catalyst support formed as a shaped body, for example a porous amorphous aluminosilicate support, formed as a sphere, based on natural sheet silicates based on natural acid-treated calcined bentonites, which is impregnated through with potassium acetate as promoter.

Such VAM shell catalysts are usually produced by the so-called chemical route in which the catalyst support is steeped in solutions of corresponding metal precursor compounds, for example by dipping the support into the solutions, or by means of the incipient wetness method (pore-filling method) in which the support is loaded with a volume of solution corresponding to its pore volume. The Pd/Au shell of the catalyst is produced for example by first steeping the catalyst support in a first step in an $Na_2PdCl_4$ solution and then in a second step fixing the Pd component with NaOH solution onto the catalyst support in the form of a Pd-hydroxide compound. In a subsequent, separate third step, the catalyst support is then steeped in an $NaAuCl_4$ solution and then the Au component is likewise fixed by means of NaOH. After the fixing of the noble-metal components in an outer shell of the catalyst support, the loaded catalyst support is then very largely washed free of chloride and Na ions, then dried, calcined and finally reduced with ethylene at 150° C. The produced Pd/Au shell is usually approximately 100 to 500 µm thick.

Usually, the catalyst support loaded with the noble metals is then loaded with potassium acetate after the fixing or reducing step wherein, rather than the loading with potassium acetate taking place only in the outer shell loaded with noble metals, the catalyst support is completely impregnated through with the promoter. A spherical support called "KA-160" from SÜD-Chemie AG based on natural acid-treated calcined bentonites, which has a BET surface area of approximately 160 m²/g, can be used for example as catalyst support.

The VAM selectivities achieved by means of the VAM shell catalysts known in the state of the art based on Pd and Au as active metals are approx. 90 mol-%, relative to the supplied ethylene, wherein the remaining 10 mol-% of the reaction products are essentially $CO_2$ which is formed by total oxidation of the organic educts/products.

To increase the activity of the VAM shell catalysts, the catalyst supports were doped with zirconium oxide for example before the noble metal deposition. For this a finished catalyst support shaped body, for example, was surface impregnated with a solution of a zirconium oxide precursor compound and the precursor compound converted into the corresponding oxide by calcining of the shaped body. Although such surface-doped catalysts are characterized by an increased activity with regard to VAM production compared with the corresponding catalysts with Pd/Au shell known in the state of the art, Zr is very expensive and there is therefore a need to find VAM catalysts with alternative cheaper doping means which increase the activity of a VAM catalyst.

It is therefore the object of the present invention to provide, starting from a shell catalyst comprising an oxidic porous catalyst support, formed as a shaped body, with an outer shell in which metallic Pd and Au are contained, a shell catalyst for producing VAM which has a relatively high activity and can be obtained relatively cheaply.

This object is achieved starting from a shell catalyst of the generic type by doping the catalyst support with at least one oxide of an element selected from the group consisting of Li, P, Ca, V, Cr, Mn, Fe, Sr, Nb, Ta, W, La and the rare-earth metals.

Surprisingly, it was discovered that the catalyst according to the invention is characterized by a relatively high VAM activity and selectivity. As the discovered doping oxides are less expensive than zirconium oxide for example, the catalyst according to the invention can also be obtained at a relatively low cost.

An oxide of an element selected from the group consisting of Li, P, Ca, V, Cr, Mn, Fe, Sr, Nb, Ta, W, La and the rare-earth metals is also called doping oxide in the following.

The catalyst support of the catalyst according to the invention can preferably also be doped with oxides of two or more elements selected from the group consisting of Li, P, Ca, V, Cr, Mn, Fe, Sr, Nb, Ta, W, La and the rare-earth metals.

It is preferred if the catalyst support is doped with a lithium oxide, preferably with $Li_2O$.

It can furthermore be preferred if the catalyst support is doped with a phosphorus oxide, preferably with $P_2O_5$ or phosphate.

It can furthermore be preferred if the catalyst support is doped with a calcium oxide, preferably with CaO.

It can furthermore be preferred if the catalyst support is doped with a vanadium oxide, preferably with $V_2O_5$.

It can furthermore be preferred if the catalyst support is doped with a chromium oxide, preferably with $Cr_2O_3$.

It can furthermore be preferred if the catalyst support is doped with a manganese oxide, preferably with $MnO_2$, $Mn_2O_3$ and/or $Mn_3O_4$.

It can furthermore be preferred if the catalyst support is doped with an iron oxide, preferably with $Fe_2O_3$.

It can furthermore be preferred if the catalyst support is doped with a strontium oxide, preferably with SrO.

It can furthermore be preferred if the catalyst support is doped with a niobium oxide, preferably with $Nb_2O_5$.

It can furthermore be preferred if the catalyst support is doped with a tantalum oxide, preferably with $Ta_2O_5$.

It can furthermore be preferred if the catalyst support is doped with a tungsten oxide, preferably with $WO_3$.

It can furthermore be preferred if the catalyst support is doped with a lanthanum oxide, preferably with $La_2O_3$.

It can furthermore be preferred if the catalyst support is doped with a cerium oxide, preferably with $CeO_2$.

It can furthermore be preferred if the catalyst support is doped with a praseodymium oxide, preferably with $PrO_2$ and/or $Pr_2O_3$.

It can furthermore be preferred if the catalyst support is doped with a neodymium oxide, preferably with $NdO_2$ and/or $Nd_2O_3$.

It can furthermore be preferred if the catalyst support is doped with a samarium oxide, preferably with $Sm_2O_3$.

It can furthermore be preferred if the catalyst support is doped with a europium oxide, preferably with EuO and/or $Eu_2O_3$.

It can furthermore be preferred if the catalyst support is doped with a gadolinium oxide, preferably with $Gd_2O_3$.

It can furthermore be preferred if the catalyst support is doped with a terbium oxide, preferably with $TbO_2$ and/or $Tb_4O_7$.

It can furthermore be preferred if the catalyst support is doped with a dysprosium oxide, preferably with $Dy_2O_3$.

It can furthermore be preferred if the catalyst support is doped with a holmium oxide, preferably with $Ho_2O_3$.

It can furthermore be preferred if the catalyst support is doped with an erbium oxide, preferably with $Er_2O_3$.

It can furthermore be preferred if the catalyst support is doped with a thulium oxide, preferably with $Tm_2O_3$.

It can furthermore be preferred if the catalyst support is doped with an ytterbium oxide, preferably with $Yb_2O_3$.

It can furthermore be preferred if the catalyst support is doped with a lutetium oxide, preferably with $Lu_2O_3$.

The above-named oxides are often present in the catalyst support, not in the form of defined oxides, but rather in the form of mixed oxides. The doping oxide can likewise be present as a mixed oxide with oxidic support material.

It can be preferred if the inner surface of the catalyst support is doped with the doping oxide. Such catalyst supports can be obtained for example by impregnating the inner surface of a porous catalyst support shaped body with a solution of a corresponding doping oxide precursor compound and then converting the desired component of the compound into an oxide, for example by calcining.

As an alternative or in addition to this, it can be provided that the doping oxide is contained evenly distributed in the framework structure of the catalyst support. As a result of the even distribution of the doping oxide in the framework structure of the catalyst support, a uniform high activity of the catalyst and also a long service life of the catalyst due to a reduced tendency towards thermal aging are ensured.

The doping oxide is preferably contained evenly distributed in the framework structure of the catalyst support. The doping oxide is preferably contained evenly distributed in a matrix comprising a porous oxidic support material, in the form of discrete oxide particles, preferably in the form of microcrystallites and/or nanocrystallites of pure oxides or mixed oxides. Alternatively, the doping oxide can be contained homogeneously distributed in the framework structure of the catalyst support, in the form of individual isolated doping oxide units. Such homogeneous distributions can be achieved for example by replacing support oxide units, such as for example silicon dioxide or aluminium oxide units, of the corresponding support materials with doping oxide units which take the place of the named support oxide units and thus form a chemical bond to the framework structure. The replacement of units of the support material can be achieved using methods known per se to a person skilled in the art, for example already during the synthesis of such support materials or by solid-state exchange.

The catalyst support of the catalyst according to the invention can be produced for example using a method comprising the steps of a) mixing a powdery oxidic porous support material with a powdery element selected from the group consisting of Li, P, Ca, V, Cr, Mn, Fe, Sr, Nb, Ta, W, La and the rare-earth metals or with a powdery compound of an element of the above-named group;

b) shaping a shaped body from the mixture obtained according to step a);

c) calcining the shaped body obtained according to step b), wherein the element or its compound, if this is not an oxide, is preferably converted into the corresponding oxide during the calcining.

The above-named method results in catalyst support shaped bodies with a solid structure of sintered-together particles of support material and doping oxide, wherein the doping oxide particles are contained evenly distributed in the particle structure.

A porous catalyst support shaped body contained in the catalyst according to the invention, for example based on an acid-treated calcined bentonite doped with iron oxide as sheet silicate can be produced e.g. by grinding a powdery (uncalcined) acid-treated bentonite with a powdery iron compound and water and then mixing it thoroughly until homogeneous, shaping the resulting mixture accompanied by compression to form a shaped body by means of devices familiar to a person skilled in the art, such as for example extruders or tablet presses, and then calcining the uncured shaped body to form a stable shaped body. The calcining is preferably carried out at temperatures at which a solid structure is obtained and optionally the iron compound is converted into iron(III) oxide. The size of the specific surface area of the doped catalyst support depends in particular on the quality of the (untreated) bentonite used, the acid-treatment method of the bentonite used, i.e. for example the nature and the quantity, relative to the bentonite, and the concentration of the inorganic acid used, the acid-treatment duration and temperature, on the moulding pressure and on the calcining duration and temperature and the calcining atmosphere.

Acid-treated bentonites can be obtained by treating bentonites with strong acids such as for example sulphuric acid, phosphoric acid or hydrochloric acid. A definition, also valid within the framework of the present invention, of the term bentonite is given in Römpp, Lexikon Chemie, $10^{th}$ edition, Georg Thieme Verlag. Bentonites particularly preferred within the framework of the present invention are natural aluminium-containing sheet silicates which contain montmorillonite (as smectite) as main mineral. After the acid treatment, the bentonite is as a rule washed with water, dried and ground to a powder.

According to a preferred embodiment of the catalyst according to the invention, it is provided that the porous oxidic catalyst support comprises a silicon oxide, aluminium oxide, aluminosilicate, zirconium oxide, titanium oxide, a natural sheet silicate, in particular an acid-treated calcined bentonite, or a mixture of two or more of the above-named oxides or is formed from one of the above-named oxides or mixtures.

By "natural sheet silicate", for which the term "phyllosilicate" is also used in the literature, is meant within the framework of the present invention treated or untreated silicate mineral from natural sources in which $SiO_4$ tetrahedra, which form the structural base unit of all silicates, are cross-linked with each other in layers of the general formula $[Si_2O_5]^{2-}$. These tetrahedron layers alternate with so-called octahedron layers in which a cation, principally Al and Mg, is octahedrally surrounded by OH or O. A distinction is drawn for example between two-layer phyllosilicates and three-layer phyllosilicates. Sheet silicates preferred within the framework of the present invention are clay minerals, in particular kaolinite, beidellite, hectorite, saponite, nontronite, mica, vermiculite and smectites, wherein smectites and in particular montmorillonite are particularly preferred. Definitions of the term "sheet silicates" are to be found for example in "Lehrbuch der anorganischen Chemie", Hollemann Wiberg, de Gruyter, $102^{nd}$ edition, 2007 (ISBN 978-3-11-017770-1) or in "Römpp Lexikon Chemie", $10^{th}$ edition, Georg Thieme Verlag under the heading "Phyllosilikat". Typical treatments to which a natural sheet silicate is subjected before use as support material include for example a treatment with acids and/or calcining. A natural sheet silicate particularly preferred within the framework of the present invention is a bentonite. Admittedly, bentonites are not really natural sheet silicates, more a mixture of predominantly clay minerals containing sheet silicates. Thus in the present case, where the natural sheet silicate is a bentonite, it is to be understood that the natural sheet silicate is present in the catalyst support in the form of or as a constituent of a bentonite.

It can furthermore be preferred if the doping oxide(s) is/are contained in the catalyst support in a proportion of 0.01 to 25 mass-%, preferably in a proportion of 0.02 to 20 mass-% and preferably in a proportion of 0.05 to 20 mass-%, relative to the mass of the catalyst support. If the doping oxide is represented in the catalyst support in a proportion of less than 0.01 mass-%, the activity-increasing properties of the corresponding oxide have only a slight effect, while above a proportion of 25 mass-% the increase in activity of the catalyst can be accompanied by a clear decrease in VAM selectivity. It can furthermore be preferred if the doping oxide(s) is/are contained in the catalyst support in a proportion of 0.5 to 25 mass-%, preferably 3 to 10 mass-%, relative to the mass of the catalyst support.

In view of a small pore diffusion limitation, it can be provided according to a further preferred embodiment of the catalyst according to the invention that the catalyst support has an average pore diameter of 8 to 50 nm, preferably from 10 to 35 nm and preferably 11 to 30 nm.

It was found that the VAM selectivity of the catalyst according to the invention depends on the integral pore volume of the catalyst support. According to a further preferred embodiment of the catalyst according to the invention, the catalyst support therefore has an integral pore volume according to BJH of between 0.25 and 0.7 ml/g, preferably between 0.3 and 0.6 ml/g and preferably between 0.35 and 0.5 ml/g.

The integral pore volume of the catalyst support is determined according to the BJH method by means of nitrogen adsorption. The surface area of the catalyst support and its integral pore volume are determined according to the BET or according to the BJH method. The BET surface area is determined according to the BET method according to DIN 66131; a publication of the BET method is also found in J. Am. Chem. Soc. 60, 309 (1938). In order to determine the surface area and the integral pore volume of the catalyst support or the catalyst, the sample can be measured for example with a fully automatic nitrogen porosimeter from Micromeritics, type ASAP 2010, by means of which an adsorption and desorption isotherm is recorded.

To determine the surface area and the porosity of the catalyst support or catalyst according to the BET theory, the data are evaluated according to DIN 66131. The pore volume is determined from the measurement data using the BJH method (E. P. Barret, L. G. Joiner, P. P. Haienda, J. Am. Chem. Soc. 73 (1951, 373)). Effects of capillary condensation are also taken into account when using this method. Pore volumes of specific pore size ranges are determined by totalling incremental pore volumes which are obtained from the evaluation of the adsorption isotherms according to BJH. The integral pore volume according to the BJH method relates to pores with a diameter of 1.7 to 300 nm.

It can be provided according to a further preferred embodiment of the catalyst according to the invention that the water absorbency of the catalyst support is 40 to 75%, preferably 50 to 70% calculated as the weight increase due to water absorption. The absorbency is determined by steeping 10 g of the support sample in deionized water for 30 min until gas bubbles no longer escape from the support sample. The excess water is then decanted and the steeped sample blotted with a cotton towel to remove adhering moisture from the sample. The water-laden support is then weighed out and the absorbency calculated as follows:

(amount weighed out $(g)$–amount weighed in $(g)$)× 10=water absorbency (%)

The acidity of the catalyst support can advantageously influence the activity of the catalyst according to the invention during the gas-phase synthesis of VAM from acetic acid and ethene. According to a further preferred embodiment of the catalyst according to the invention the catalyst support has an acidity of between 1 and 150 µval/g, preferably between 5 and 130 µval/g, preferably between 10 and 100 µval/g and particularly preferably between 10 and 60 µval/g. The acidity of the catalyst support is determined as follows: 100 ml water (with a pH blank value) is added to 1 g of the finely ground catalyst support and extraction carried out for 15 minutes accompanied by stirring. Titration to at least pH 7.0 with 0.01 n NaOH solution follows, wherein the titration is carried out stepwise; 1 ml of the NaOH solution is firstly added dropwise to the extract (1 drop/second), followed by a 2-minute wait, the pH is read, a further 1 ml NaOH added dropwise, etc. The blank value of the water used is determined and the acidity calculation corrected accordingly.

The titration curve (ml 0.01 NaOH against pH) is then plotted and the intersection point of the titration curve at pH 7 determined. The mole equivalents which result from the NaOH consumption for the intersection point at pH 7 are calculated in $10^{-6}$ equiv/g support.

Total acid:

$$\frac{10 * \text{ml } 0.01 \, n \text{ NaOH}}{1 \text{ Support}} = \mu\text{val/g}$$

It has been established that, the smaller the surface area of the catalyst support, the higher the VAM selectivity of the catalyst according to the invention. In addition, the smaller the surface area of the catalyst support is, the greater the chosen thickness of the Pd/Au shell can be, without appreciable losses of VAM selectivity. According to a preferred embodiment of the catalyst according to the invention, the surface of the catalyst support therefore has a surface area of less than/equal to 160 m$^2$/g, preferably less than 140 m$^2$/g, preferably less than 135 m$^2$/g, further preferably less than 120 m$^2$/g, more preferably less than 100 m$^2$/g, still more preferably less than 80 m$^2$/g and particularly preferably less than 65 m$^2$/g. By "surface area" of the catalyst support is meant within the framework of the present invention the BET surface area of the support which is determined by means of adsorption of nitrogen according to DIN 66132.

According to a further preferred embodiment of the catalyst according to the invention, it can be provided that the catalyst support has a surface area of 160 to 40 m$^2$/g, preferably between 140 and 50 m$^2$/g, preferably between 135 and 50 m$^2$/g, further preferably between 120 and 50 m$^2$/g, more preferably between 100 and 50 m$^2$/g and most preferably between 100 and 60 m$^2$/g.

The catalyst according to the invention is usually produced by subjecting a plurality of catalyst support shaped bodies to a "batch" method during the individual method steps of which the shaped bodies are for example subjected to relatively high mechanical load stresses communicated by stirring and mixing tools. In addition, the catalyst according to the invention can be subjected to a strong mechanical load stress during the filling of a reactor, which can result in an undesired formation of dust and damage to the catalyst support, in particular to its catalytically active shell lying in an outer area. In particular to keep the wear of the catalyst according to the invention within reasonable limits, the catalyst has a hardness greater than/equal to 20 N, preferably greater than/equal to 25 N, further preferably greater than/equal to 35 N and most preferably greater than/equal to 40 N. The hardness is ascertained by means of an 8M tablet-hardness testing machine from Dr. Schleuniger Pharmatron AG, determining the average for 99 shell catalysts after drying of the catalyst at 130° C. for 2 h, wherein the apparatus settings are as follows:

| | |
|---|---|
| Hardness: | N |
| Distance from the shaped body: | 5.00 mm |
| Time delay: | 0.80 s |
| Feed type: | 6 D |
| Speed: | 0.60 mm/s |

The hardness of the catalyst can be influenced for example by varying certain parameters of the method for producing the catalyst support, for example through the selection of the raw materials, the calcining duration and/or the calcining temperature of an uncured shaped body formed from a corresponding support mixture, or by particular loading materials, such as for example methyl cellulose or magnesium stearate.

The catalyst according to the invention comprises a doped catalyst support formed as a shaped body, preferably based on a natural sheet silicate, in particular based on an acid-treated calcined bentonite. By "based on" is meant that the catalyst support comprises a natural sheet silicate. It can be preferred if the proportion of natural sheet silicate in the catalyst support is greater than/equal to 50 mass-%, preferably greater than/equal to 60 mass-%, preferably greater than/equal to 70 mass-%, further preferably greater than/equal to 80 mass-%, more preferably greater than/equal to 90 mass-% and most preferably greater than/equal to 95 mass-%, relative to the mass of the doped catalyst support.

It can be preferred according to a further preferred embodiment of the catalyst according to the invention if at least 80%, preferably at least 85% and preferably at least 90%, of the integral pore volume of the catalyst support according to BJH is formed from mesopores and macropores. This counteracts a reduced activity, effected by diffusion limitation, of the catalyst according to the invention, in particular with relatively thick Pd/Au shells. By micropores, mesopores and macropores are meant in this case pores which have a diameter of less than 2 nm, a diameter of 2 to 50 nm and a diameter of more than 50 nm respectively.

The catalyst support of the catalyst according to the invention can have a bulk density of more than 0.3 g/ml, preferably more than 0.35 g/ml and particularly preferably a bulk density of between 0.35 and 0.6 g/ml.

In order to ensure an adequate chemical stability of the catalyst according to the invention, the sheet silicate contained in the support has an SiO$_2$ content of at least 65 mass-%, preferably at least 80 mass-% and preferably 95 to 99.5 mass-%, relative to the mass of the sheet silicate.

In the gas-phase synthesis of VAM from acetic acid and ethene, a relatively low Al$_2$O$_3$ content in the sheet silicate is scarcely disadvantageous, whereas with high Al$_2$O$_3$ contents a marked reduction in indentation hardness must be expected. According to a preferred embodiment of the catalyst according to the invention, the sheet silicate therefore contains less than 10 mass-% Al$_2$O$_3$, preferably 0.1 to 3 mass-% and preferably 0.3 to 1.0 mass-%, relative to the mass of the sheet silicate.

The acidity of the catalyst support can advantageously influence the activity of the catalyst according to the invention during the gas-phase synthesis of VAM from acetic acid and ethene. According to a further preferred embodiment of the catalyst according to the invention, the catalyst support has an acidity of between 1 and 150 μval/g, preferably between 5 and 130 μval/g and particularly preferably between 10 and 100 μval/g.

The catalyst support of the catalyst according to the invention is formed as a shaped body. The catalyst support can in principle assume the form of any geometric body to which a corresponding noble metal shell can be applied. However, it is preferred if the catalyst support is formed as a sphere, cylinder (also with rounded end surfaces), perforated cylinder (also with rounded end surfaces), trilobe, "capped tablet", tetralobe, ring, doughnut, star, cartwheel, "reverse" cartwheel, or as a strand, preferably as a ribbed strand or star strand, preferably as a sphere.

The diameter or the length and thickness of the catalyst support of the catalyst according to the invention is preferably 2 to 9 mm, depending on the geometry of the reactor tube in which the catalyst is to be used. If the catalyst support is formed as a sphere, then the catalyst support preferably has a diameter of more than 2 mm, preferably a diameter of more than 3 mm and preferably a diameter of 4 mm to 9 mm.

In general, the smaller the thickness of the Pd/Au shell of the catalyst, the higher the VAM selectivity of the catalyst according to the invention. According to a further preferred embodiment of the catalyst according to the invention, the shell of the catalyst therefore has a thickness of less than 300 μm, preferably less than 200 μm, preferably less than 150 μm, further preferably less than 100 μm and more preferably less than 80 μm. The thickness of the shell can be measured visually by means of a microscope. The area in which the noble metals are deposited appears black, while the areas free of noble metals appear white. As a rule, the boundary between areas containing noble metals and areas free of them is very sharp and can clearly be recognized visually. If the above-named boundary is not sharply defined and accordingly not clearly recognizable visually, the thickness of the shell corresponds to the thickness of a shell, measured starting from the outer surface of the catalyst support, which contains 95% of the noble metal deposited on the support.

However, it was likewise found that in the case of the catalyst according to the invention the Pd/Au shell can be formed with a relatively large thickness effecting a high activity of the catalyst, without effecting an appreciable reduction of the VAM selectivity of the catalyst according to the invention. According to another preferred embodiment of the catalyst according to the invention, the shell of the catalyst therefore has a thickness of between 200 and 2000 μm, preferably between 250 and 1800 μm, preferably between 300 and 1500 μm and further preferably between 400 and 1200 μm.

In order to ensure an adequate activity of the catalyst according to the invention, the proportion of Pd in the catalyst is 0.6 to 2.5 mass-%, preferably 0.7 to 2.3 mass-% and preferably 0.8 to 2 mass-%, relative to the mass of the catalyst support loaded with noble metal.

It can also be preferred if the catalyst according to the invention has a Pd content of 1 to 20 g/l, preferably 2 to 15 g/l and preferably 3 to 10 g/l.

In order to likewise ensure an adequate activity and selectivity of the catalyst according to the invention, the Au/Pd atomic ratio of the catalyst is preferably between 0 and 1.2, preferably between 0.1 and 1, preferably between 0.3 and 0.9 and particularly preferably between 0.4 and 0.8.

In addition it can be preferred if the catalyst according to the invention has an Au content of 1 to 20 g/l, preferably 1.5 to 15 g/l and preferably 2 to 10 g/l.

In order to ensure a largely uniform activity of the catalyst according to the invention over the thickness of the Pd/Au shell, the noble-metal concentration should vary only relatively little over the shell thickness. It is therefore preferred if, over an area of 90% of the shell thickness, the area being at a distance of 5% of the shell thickness from each of the outer and inner shell limit, the profile of the noble-metal concentration of the catalyst varies from the average noble-metal concentration of this area by a maximum of +/−20%, preferably by a maximum of +/−15% and preferably by a maximum of +/−10%. Such profiles can be obtained by the spraying, described below, onto a fluidized bed.

Chloride poisons the catalyst according to the invention and leads to a deactivation of same. According to a further preferred embodiment of the catalyst according to the invention, its chloride content is therefore less than 250 ppm, preferably less than 150 ppm.

The catalyst according to the invention preferably contains, in addition to the doping oxide(s), at least one alkali metal compound as a further promoter, preferably a potassium, sodium, caesium or rubidium compound, preferably a potassium compound. Suitable and particularly preferred potassium compounds include potassium acetate KOAc, potassium carbonate $K_2CO_3$, potassium hydrogen carbonate $KHCO_3$, potassium formate KOOCMe and potassium hydroxide KOH and also all potassium compounds which become K acetate KOAc under the respective reaction conditions of VAM synthesis. The potassium compound can be deposited on the catalyst support both before and after the reduction of the metal components into the metals Pd and Au. According to a further preferred embodiment of the catalyst according to the invention, the catalyst comprises an alkali metal acetate, preferably potassium acetate. It is particularly preferred in order to ensure an adequate promoter activity if the alkali metal acetate content of the catalyst is 0.1 to 0.7 mol/l, preferably 0.3 to 0.5 mol/l.

According to a further preferred embodiment of the catalyst according to the invention, the alkali metal/Pd atomic ratio is between 1 and 12, preferably between 2 and 10 and particularly preferably between 4 and 9. Preferably, the smaller the surface area of the catalyst support, the lower the alkali metal/Pd atomic ratio.

The present invention also relates to a first method for producing a shell catalyst, in particular a shell catalyst according to the invention, comprising the steps of a) providing an oxidic porous catalyst support, formed as a shaped body, which is doped with at least one oxide of an element selected from the group consisting of Li, P, Ca, V, Cr, Mn, Fe, Sr, Nb, Ta, W, La and the rare-earth metals;

b) depositing a solution of a Pd precursor compound onto the catalyst support;

c) depositing a solution of an Au precursor compound onto the catalyst support;

d) converting the Pd component of the Pd precursor compound into the metal form;

e) converting the Au component of the Au precursor compound into the metal form.

In principle, any Pd or Au compound by means of which a high degree of dispersion of the metals can be achieved can be used as Pd and Au precursor compound. By "degree of dispersion" is meant the ratio of the number of all the surface metal atoms of all the metal/alloy particles of a supported metal catalyst to the total number of all the metal atoms of the metal/alloy particles. In general it is preferred if the degree of dispersion corresponds to a relatively high numerical value, since in this case as many metal atoms as possible are freely accessible for a catalytic reaction. This means that, given a relatively high degree of dispersion of a supported metal catalyst, a specific catalytic activity of same can be achieved with a relatively small quantity of metal used. According to a further preferred embodiment of the catalyst according to the invention, the degree of dispersion of the palladium is 1 to 30%.

It can be preferred to select the Pd and Au precursor compounds from the halides, in particular chlorides, oxides, nitrates, nitrites, formates, propionates, oxalates, acetates, hydroxides, hydrogen carbonates, amine complexes or organic complexes, for example triphenylphosphine complexes or acetylacetonate complexes, of these metals.

Examples of preferred Pd precursor compounds are water-soluble Pd salts. According to a particularly preferred embodiment of the method according to the invention, the Pd precursor compound is selected from the group consisting of $Pd(NH_3)_4(OH)_2$, $Pd(NH_3)_4(OAc)_2$, $H_2PdCl_4$, $Pd(NH_3)_4(HCO_3)_2$, $Pd(NH_3)_4(HPO_4)$, $Pd(NH_3)_4Cl_2$, $Pd(NH_3)_4$ oxalate, Pd oxalate, $Pd(NO_3)_2$, $Pd(NH_3)_4(NO_3)_2$, $K_2Pd(OAc)_2(OH)_2$, $Pd(NH_3)_2(NO_2)_2$, $K_2Pd(NO_2)_4$, $Na_2Pd(NO_2)_4$, $Pd(OAc)_2$, $PdCl_2$, $K_2PdCl_4$ and $Na_2PdCl_4$. Instead of the amine complexes, the corresponding ethylenediamine or ethanolamine complexes can also be used. In addition to $Pd(OAc)_2$ other carboxylates of palladium can also be used, preferably the salts of the aliphatic monocarboxylic acids with 3 to 5 carbon atoms, for example the propionate or butyrate salt.

According to a further preferred embodiment of the method according to the invention, Pd nitrite precursor compounds can also be preferred. Preferred Pd nitrite precursor compounds are for example those which are obtained by dissolving $Pd(OAc)_2$ in an $NaNO_2$ solution.

Examples of preferred Au precursor compounds are water-soluble Au salts. According to a particularly preferred embodiment of the method according to the invention, the Au precursor compound is selected from the group consisting of $KAuO_2$, $HAuCl_4$, $KAu(NO_2)_4$, $AuCl_3$, $NaAuCl_4$, $KAu(OAc)_3(OH)$, $HAu(NO_3)_4$, $NaAuO_2$, $NMe_4AuO_2$, $RbAuO_2$, $CsAuO_2$, $NaAu(OAc)_3(OH)$, $RbAu(OAc)_3OH$, $CsAu(OAc)_3OH$, $NMe_4Au(OAc)_3OH$, $KAuCl_4$ and $Au(OAc)_3$. It is recommended where appropriate to produce fresh $Au(OAc)_3$ or $KAuO_2$ each time by precipitating the oxide/hydroxide from a gold acid solution, washing and isolating the precipitate and taking up same in acetic acid or KOH.

All pure solvents or solvent mixtures in which the selected precursor compounds are soluble and which, after application to the catalyst support, can be easily removed again from same by means of drying are suitable as solvents for the precursor compounds. Preferred solvent examples for the metal acetates as precursor compounds are above all acetone or unsubstituted carboxylic acids, in particular acetic acid, and for the metal chlorides above all water or dilute hydrochloric acid.

If the precursor compounds are not sufficiently soluble in acetone, acetic acid, water or dilute hydrochloric acid or mixtures thereof, other solvents can also be used as an alternative or in addition to the named solvents. Solvents which are inert and miscible with acetic acid or water preferably come into consideration as other solvents in this case. Ketones, for example acetone or acetylacetone, furthermore ethers, for example tetrahydrofuran or dioxan, acetonitrile, dimethylformamide and solvents based on hydrocarbons such as for example benzene may be named as preferred solvents which are suitable for adding to acetic acid.

Ketones, for example acetone, or alcohols, for example ethanol or isopropanol or methoxyethanol, lyes, such as aqueous KOH or NaOH, or organic acids, such as acetic acid, formic acid, citric acid, tartaric acid, malic acid, glyoxylic acid, glycolic acid, oxalic acid, oxamic acid, amino acids, pyruvic acid or lactic acid may be named as preferred solvents or additives which are suitable for adding to water.

If chloride compounds are used as precursor compounds, it must be ensured that the chloride ions are reduced to a tolerable residual quantity before using the catalyst produced according to the method according to invention, since chloride is a catalyst poison. For this, the catalyst support is as a rule washed with plenty of water after the fixing of the Pd and Au component of the Pd or Au precursor compound onto the catalyst support. In general, this happens either immediately after the fixing by hydroxide precipitation of the Pd and Au component by means of lye, after the fixing by acid precipitation or after the reduction of the noble-metal components to the respective metal/alloy.

However, according to a preferred embodiment of the method according to the invention, chloride-free Pd and Au precursor compounds are used as well as chloride-free solvents to keep the chloride content in the catalyst as low as possible and avoid a laborious washing free of chloride. The corresponding acetate, hydroxide or nitrite compounds are preferably used as precursor compounds, as they contaminate the catalyst support with chloride to only a very small extent.

The deposition of the Pd and Au precursor compounds onto the catalyst support in the area of an outer shell of the catalyst support can be achieved according to methods known per se. Thus the precursor solutions can be deposited by steeping, by dipping the support into the precursor solutions or steeping it according to the incipient wetness method. A base, for example caustic soda solution or potash lye, is then deposited on the catalyst support, whereby the noble-metal components are precipitated onto the support in the form of hydroxides. It is also possible for example to firstly steep the support in lye and then apply the precursor compounds to the thus-pretreated support.

According to a further preferred embodiment of the method according to the invention, it is therefore provided that the Pd and the Au precursor compound are deposited onto the catalyst support by steeping the catalyst support in the solution of the Pd precursor compound and in the solution of the Au precursor compound or in a solution which contains both the Pd and the Au precursor compound.

According to the state of the art, the active metals Pd and Au, starting from chloride compounds in the area of a shell of the support, are applied to same by means of steeping. However, this technique has reached its limits as regards minimum shell thicknesses and maximum Au loading. The minimum shell thickness of the corresponding known VAM catalysts is at best approx. 100 µm and it is not foreseen that even thinner shells can be obtained by means of steeping. In addition, higher Au loadings within the desired shell by means of steeping can be achieved only with difficulty, since the Au precursor compounds tend to diffuse from the shell into inner zones of the catalyst support shaped body, which results in broad Au shells, areas of which contain very little Pd.

The active metals, or, put another way, their precursor compounds, can also be deposited on the support for example by means of so-called physical processes. For this, the support can according to the invention preferably be sprayed for example with a solution of the precursor compounds, wherein the catalyst support is moved in a coating drum into which hot air is blown, with the result that the solvent quickly evaporates.

But according to a further preferred embodiment of the method according to the invention, it is provided that the solution of the Pd precursor compound and the solution of the Au precursor compound are deposited onto the catalyst support by spraying the solutions onto a fluid bed or a fluidized bed of the catalyst support, preferably by means of an aerosol of the solutions. The shell thickness can thereby be continuously adjusted and optimized, for example up to a thickness of 2 mm. But even very thin noble-metal shells with a thickness of less than 100 µm are thus possible.

The above-named embodiment of the method according to the invention is preferably carried out by means of a fluidized bed in a fluidized bed unit. It is particularly preferred if the unit contains a so-called controlled air-glide layer. For one thing, the catalyst support shaped bodies are thoroughly mixed by the controlled air-glide layer, wherein they simultaneously rotate about their own axis, whereby they are dried evenly by the process air. For another, due to the consequent orbital movement, effected by the controlled air-glide layer, of the shaped bodies the catalyst support shaped bodies pass through the spray procedure (application of the precursor compounds) at a virtually constant frequency. A largely uniform shell thickness of a treated batch of shaped bodies is thereby achieved. A further result is that the noble-metal concentration varies only relatively slightly over a relatively large area of the shell thickness, i.e. the noble-metal concentration describes an approximately rectangular function over a large area of the shell thickness, whereby a largely uniform activity of the resulting catalyst is ensured over the thickness of the Pd/Au shell.

It is preferred if the shaped bodies circulate elliptically or toroidally in the fluidized bed. To give an idea of how the shaped bodies move in such fluidized beds, it may be stated that in the case of "elliptical circulation" the catalyst support shaped bodies move in the fluidized bed in a vertical plane on an elliptical path, the size of the major and minor axis changing. In the case of "toroidal circulation" the catalyst support shaped bodies move in the fluidized bed in the vertical plane on an elliptical path, the size of the major and minor axis changing, and in the horizontal plane on a circular path, the size of the radius changing. On average, the shaped bodies move in the case of "elliptical circulation" in the vertical plane on an elliptical path, in the case of "toroidal circulation" on a toroidal path, i.e. a shaped body covers the surface of a torus helically with a vertically elliptical section.

Suitable coating drums, fluid bed units and fluidized bed units for carrying out the method according to the invention according to preferred embodiments are known in the state of the art and sold e.g. by Heinrich Brucks GmbH (Alfeld, Germany), ERWEK GmbH (Heusenstamm, Germany), Stechel (Germany), DRIAM Anlagenbau GmbH (Eriskirch, Germany), Glatt GmbH (Binzen, Germany), G.S. Divisione Verniciatura (Osteria, Italy), HOFER-Pharma Maschinen GmbH (Weil am Rhein, Germany), L. B. Bohle Maschinen+Verfahren GmbH (Enningerloh, Germany), Lödige Maschinenbau GmbH (Paderborn, Germany), Manesty (Merseyside, United Kingdom), Vector Corporation (Marion, Iowa, USA), Aeromatic-Fielder AG (Bubendorf, Switzerland), GEA Process Engineering (Hampshire, United Kingdom), Fluid Air Inc. (Aurora, Ill., USA), Heinen Systems GmbH (Varel, Germany), Hüttlin GmbH (Steinen, Germany), Umang Pharmatech Pvt. Ltd. (Marharashtra, India) and Innojet Technologies (Lörrach, Germany). Particularly preferred fluidized bed equipment is sold by Innojet Technologies under the names Innojet® Aircoater or Innojet® Ventilus.

According to a further preferred embodiment of the method according to the invention, the catalyst support is heated during the deposition of the solutions, for example by means of heated process air. The drying-off speed of the deposited solutions of the noble-metal precursor compounds can be determined via the degree of heating of the catalyst supports. At relatively low temperatures the drying-off speed is for example relatively low, with the result that with a corresponding quantitative deposition, greater shell thicknesses can be formed because of the high diffusion of the precursor compounds that is caused by the presence of solvent. At relatively high temperatures the drying-off speed is for example relatively high, with the result that solution of the precursor compounds coming into contact with the shaped body almost immediately dries off, which is why solution deposited on the catalyst support cannot penetrate deep into the latter. At relatively high temperatures relatively small shell thicknesses can thus be obtained with a high noble-metal loading. For example the catalyst support can be heated to a temperature of 40 to 80° C.

With the methods described in the state of the art for producing VAM shell catalysts based on Pd and Au, commercially available solutions of the precursor compounds such as $Na_2PdCl_4$, $NaAuCl_4$ or $HAuCl_4$ solutions are customarily used. In the more recent literature, as already stated previously, chloride-free Pd or Au precursor compounds such as for example $Pd(NH_3)_4(OH)_2$, $Pd(NH_3)_2(NO_2)_2$ and $KAuO_2$ are also used. These precursor compounds react base in solution, while the standard chloride, nitrate and acetate precursor compounds all react acid in solution.

To deposit the precursor compounds onto the catalyst support, preferably aqueous $Na_2PdCl_4$ and $NaAuCl_3$ solutions are customarily used. These metal-salt solutions are normally applied to the support at room temperature and the metal components then fixed with NaOH as insoluble Pd or Au hydroxides. Then the loaded support is customarily washed free of chloride with water. In particular the Au fixing has disadvantages, such as long action times of the base in order to induce the precipitation of the stable Au tetrachloro complex, incomplete precipitation and concomitant inadequate Au retention.

According to a further preferred embodiment of the method according to the invention, the method comprises the steps in which a) a first solution of a Pd and/or an Au precursor compound is provided;

b) a second solution of a Pd and/or an Au precursor compound is provided, wherein the first solution effects a precipitation of the noble-metal component(s) of the precursor compound(s) of the second solution and vice versa;

c) the first solution and the second solution are deposited onto the catalyst support.

This embodiment of the method according to the invention uses two different precursor solutions, of which for example one contains a Pd, and the other an Au, precursor compound. Generally, one of the solutions preferably has a basic, and the other an acid, pH. Generally, the solutions are deposited onto the catalyst support by firstly impregnating the support with the first and then in a subsequent step with the second solution, as described previously, by steeping. Upon deposition of the second solution the two solutions are then combined on the support, whereby the pH of the solutions changes and the Pd or Au component of the respective precursor compound is precipitated onto the support, without an auxiliary base customary in the state of the art, such as NaOH or KOH, needing to be applied to the support.

The named embodiment of the method according to the invention is thus based on an impregnation of the catalyst support with the first solution of a Pd and/or Au precursor compound and the second solution of a Pd and/or Au precursor compound, wherein the two solutions are incompatible with one another, i.e. the first solution effects a precipitation of the noble-metal component(s) of the precursor compound (s) of the second solution and vice versa, with the result that in the contact zone of the two solutions both the pre-impregnated Pd/Au component(s) and the post-impregnated Pd/Au component(s) precipitate almost simultaneously and thus lead to an intimate thorough mixing of Pd/Au. Drying can optionally take place between the two impregnation steps.

Suitable aqueous solutions of Pd precursor compounds for the impregnation with incompatible solutions are listed by way of example in Table 1.

TABLE 1

| Precursor compound | Character of the solution |
| --- | --- |
| $PdCl_2$ | acid |
| $Pd(NH_3)_2(NO_2)_2$ | basic |
| $Na_2PdCl_4$ | neutral |
| $Pd(NH_3)_4(OH)_2$ | basic |
| $Pd(NO_3)_2$ | acid |
| $K_2Pd(OAc)_2(OH)_2$ | basic through dissolution of palladium acetate in KOH |

If, with regard to a premature Au reduction, $NH_3$ were to have too strong a reductive effect, it is also possible to use the corresponding diamine complexes with ethylenediamine as ligand or the corresponding ethanol amine complexes instead of the palladium amine complexes.

Suitable aqueous solutions of Au precursor compounds for the impregnation with incompatible solutions are listed by way of example in Table 2.

TABLE 2

| Precursor compound | Character of the solution |
| --- | --- |
| $AuCl_3$ | acid |
| $KAuO_2$ | basic through dissolution of $Au(OH)_3$ in KOH |
| $NaAuCl_4$ | neutral |
| $HAuCl_4$ | acid |
| $KAu(OAc)_3(OH)$ | basic through dissolution of $Au(OAc)_3$ in KOH |
| $HAu(NO_3)_4$ | acid (stable in semi-concentrated $HNO_3$) |

Suitable combinations of incompatible solutions for the base-free precipitation of the noble-metal components are for example a $PdCl_2$ and a $KAuO_2$ solution; a $Pd(NO_3)_2$ and a $KAuO_2$ solution; a $Pd(NH_3)_4(OH)_2$ and an $AuCl_3$ or $HAuCl_4$ solution.

According to a further preferred embodiment of the method according to the invention Pd can also be precipitated with incompatible Pd solutions and analogously Au with incompatible Au solutions, e.g. by bringing a $PdCl_2$ solution into contact with a $Pd(NH_3)_4(OH)_2$ solution or an $HAuCl_4$ with a $KAuO_2$ solution. In this way high Pd and/or Au contents can precipitate in the shell without having to use highly-concentrated solutions.

According to a further embodiment of the method according to the invention mixed solutions compatible with one another can also be used which are brought into contact with a solution incompatible with the mixed solution, for the noble-metal precipitation. An example of a mixed solution is a $PdCl_2$ and $AuCl_3$-containing solution, the noble-metal components of which can be precipitated with a $KAuO_2$ solution, or a $Pd(NH_3)_4(OH)_2$ and $KAuO_2$-containing solution, the noble-metal components of which can be precipitated with a $PdCl_2$ and $HAuCl_4$-containing solution. A further example of a mixed solution is the $HAuCl_4$ and $KAuO_2$ pairing.

The impregnation with the incompatible solutions will preferably take place by means of steeping or by means of spray impregnation, wherein the incompatible solutions are for example sprayed simultaneously through one or more double nozzle(s) or simultaneously by means of two nozzles or nozzle groups or sequentially by means of one or more nozzle(s).

Because of the rapid immobilization (fixing) of the metal components of the precursor compounds in the shell and the concomitant shortened Pd and Au diffusion, the impregnation with the incompatible solutions can lead to thinner shells than the conventional use of solutions compatible with one another. By means of the incompatible solutions, high noble-metal contents in thin shells, improved metal retention, more rapid and more complete precipitation of the noble metals, the reduction of the disruptive residual Na content of the support, the simultaneous fixing of Pd and Au in only one fixing step and the absence of NaOH costs and NaOH handling and an avoidance of a mechanical weakening of the support through the contact with excess NaOH can be achieved.

By means of the impregnation with incompatible solutions, greater noble-metal contents can be precipitated on the catalyst support through a single fixing step which comprises just the deposition of two incompatible solutions than is possible with standard base (NaOH) fixing.

In particular, high Au contents with an Au/Pd atomic ratio of 0.6 and more, which is very desirable with regard to the increase in VAM selectivity, can be easily achieved by means of the principle of the incompatible solutions.

According to a further preferred embodiment of the method according to the invention it is provided that, for the fixing of the noble-metal component(s) of the precursor compound(s) onto the catalyst support, the catalyst support is subjected to a fixing step, after the Pd and/or the Au precursor compound has/have been deposited onto the catalyst support. The fixing step can comprise the treatment of the support with lye or acid, depending on whether the precursor compound is acid or basic, or a calcining of the support for converting the noble-metal component(s) into a hydroxide compound(s) or into an oxide. The fixing step can also be omitted and the noble-metal components directly reduced, e.g. by treatment with a reductive gas phase, e.g. ethylene, etc., at increased temperatures of 20° C. to 200° C.

It is likewise possible to produce the catalyst according to the invention by means of a suitably doped powdery oxidic porous support material, wherein the support material is loaded with a Pd and an Au precursor compound or with Pd and Au particles. The pre-treated support material can be coated in the form of a washcoat onto a suitable support structure, for example a sphere of steatite or a KA-160 support from SÜD-Chemie AG, and then processed further into the catalyst by calcining and optionally reduction.

Accordingly the invention relates to a second method for producing a shell catalyst, in particular a shell catalyst according to the invention, comprising the steps of a) providing a powdery oxidic porous support material which is doped with at least one oxide of an element selected from the group consisting of Li, P, Ca, V, Cr, Mn, Fe, Sr, Nb, Ta, W, La and the rare-earth metals, wherein the support material is loaded with a Pd and an Au precursor compound or with Pd and Au particles;

b) depositing the loaded support material onto a support structure in the form of a shell;

c) calcining the loaded support structure from step b);

d) optionally converting the Pd and the Au component of the Pd or Au precursor compound into the metal form.

Alternatively the named method can also be carried out by firstly depositing the noble-metal-free doped support material onto a support structure and only then applying the noble metals.

After loading with the precursor compounds or after fixing the noble-metal components the support can be calcined to convert the noble-metal components into the corresponding oxides. Calcining takes place preferably at temperatures of less than 700° C., particularly preferably between 300-450° C. in the presence of air. The calcining time depends on the calcining temperature and is preferably chosen in the range of 0.5-6 hours. At a calcining temperature of approx. 400° C., the calcining time is preferably 1-2 hours. At a calcining temperature of 300° C., the calcining time is preferably up to 6 hours.

The noble-metal components are further reduced before the use of the catalyst, wherein the reduction can be carried out in situ, i.e. in the process reactor, or else ex situ, i.e. in a special reduction reactor. Reduction in situ is preferably carried out with ethylene (5 vol.-%) in nitrogen at a temperature of approx. 150° C. over a period of for example 5 hours. Reduction ex situ can be carried out for example with 5 vol.-% hydrogen in nitrogen, for example by means of forming gas, at temperatures in the range of preferably 150-500° C. over a period of 5 hours.

Gaseous or vaporable reducing agents such as for example CO, $NH_3$, formaldehyde, methanol and hydrocarbons can likewise be used, wherein the gaseous reducing agents can also be diluted with inert gas, such as for example carbon dioxide, nitrogen or argon. A reducing agent diluted with inert gas is preferably used. Mixtures of hydrogen with nitrogen or argon, preferably with a hydrogen content between 1 vol.-% and 15 vol.-%, are preferred.

The reduction of the noble metals can also be undertaken in the liquid phase, preferably by means of the reducing agents hydrazine, K-formate, $H_2O_2$, Na-formate, formic acid, ammonium formate, K-hypophosphite, hypophosphoric acid or Na-hypophosphite.

The quantity of reducing agent is preferably chosen such that during the treatment period at least the equivalent required for complete reduction of the noble-metal components is passed over the catalyst. Preferably, however, an excess of reducing agent is passed over the catalyst in order to ensure a rapid and complete reduction.

The reduction is preferably pressureless, i.e. at an absolute pressure of approx. 1 bar. For the production of industrial quantities of catalyst according to the invention a rotary tube oven or fluid-bed reactor is preferably used in order to ensure an even reduction of the catalyst.

The invention also relates to the use of the catalyst according to the invention as an oxidation catalyst, as a hydrogenation/dehydrogenation catalyst, as a catalyst in hydrogenating desulphurization, as a hydrodenitrification catalyst, as a hydrodeoxidation catalyst or as a catalyst in the synthesis of alkenylalkanoates, in particular in the synthesis of vinyl acetate monomer, in particular in the gas-phase oxidation of ethylene and acetic acid to vinyl acetate monomer.

The catalyst according to the invention is preferably used for producing VAM. Generally this takes place by passing acetic acid, ethylene and oxygen or oxygen-containing gases over the catalyst according to the invention at temperatures of 100-200° C., preferably 120-200° C., and at pressures of 1-25 bar, preferably 1-20 bar, wherein non-reacted educts can be recycled. Expediently, the oxygen concentration is kept below 10 vol.-%. Under certain circumstances, however, a dilution with inert gases such as nitrogen or carbon dioxide is also advantageous. Carbon dioxide is particularly suitable for dilution, since it is formed in small quantities in the course of VAM synthesis. The formed vinyl acetate is isolated with the help of suitable methods, which are described for example in U.S. Pat. No. 5,066,365 A.

The present invention also relates to a porous catalyst support, comprising a natural sheet silicate, in particular an acid-treated calcined bentonite, wherein the catalyst support is doped with at least one oxide of an element selected from the group consisting of Li, P, Ca, V, Cr, Mn, Fe, Sr, Nb, Ta, W, La and the rare-earth metals.

With regard to the following preferred embodiments of the catalyst support according to the invention, the above statements and explanations apply analogously to the corresponding embodiments of the shell catalyst according to the invention.

It is preferred if the inner surface of the catalyst support is doped with the doping oxide.

As an alternative or in addition to this, it can be provided that the doping oxide is contained evenly distributed in the framework structure of the catalyst support.

It is furthermore preferred if the doping oxide is contained in the catalyst support in a proportion of 0.01 to 25 mass-%, preferably in a proportion of 0.02 to 20 mass-% and preferably in a proportion of 0.05 to 20 mass-%, relative to the mass of the (doped) catalyst support.

It is also preferred if the catalyst support has an average pore diameter of 8 to 50 nm, preferably from 10 to 35 nm and preferably 11 to 30 nm.

In addition, it is preferred if the catalyst support has an integral pore volume according to BJH of between 0.25 and 0.7 ml/g, preferably between 0.3 and 0.6 ml/g and preferably 0.35 to 0.5 ml/g.

It is further preferred if the catalyst support has an acidity of between 1 and 150 µval/g, preferably between 5 and 130 µval/g, preferably between 10 and 100 µval/g and particularly preferably between 10 and 60 µval/g.

It is further preferred if the catalyst support has a surface area of less than/equal to 160 $m^2$/g, preferably less than 140 $m^2$/g, preferably less than 135 $m^2$/g, further preferably less than 120 $m^2$/g, more preferably less than 100 $m^2$/g, still more preferably less than 80 $m^2$/g and particularly preferably less than 65 $m^2$/g.

It is also preferred if the catalyst support has a surface area of 160 to 40 $m^2$/g, preferably between 140 and 50 $m^2$/g, preferably between 135 and 50 $m^2$/g, further preferably between 120 and 50 $m^2$/g, more preferably between 100 and 50 $m^2$/g and most preferably between 100 and 60 $m^2$/g.

It is furthermore preferred if the catalyst support comprises the sheet silicate in a proportion of greater than/equal to 50 mass-%, preferably greater than/equal to 60 mass-%, preferably greater than/equal to 70 mass-%, further preferably greater than/equal to 80 mass-%, more preferably greater than/equal to 90 mass-% and most preferably greater than/equal to 95 mass-%, relative to the mass of the catalyst support.

In addition, it is preferred if at least 80%, preferably at least 85% and preferably at least 90%, of the integral pore volume of the catalyst support is formed from mesopores and macropores.

It is also preferred if the catalyst support has a bulk density of more than 0.3 g/ml, preferably more than 0.35 g/ml and particularly preferably a bulk density of between 0.35 and 0.6 g/ml.

It is further preferred if the sheet silicate contained in the catalyst support has an $SiO_2$ content of at least 65 mass-%, preferably at least 80 mass-% and preferably 95 to 99.5 mass-%.

In addition, it is preferred if the sheet silicate contained in the support contains less than 10 mass-% $Al_2O_3$, preferably 0.1 to 3 mass-% and preferably 0.3 to 1.0 mass-%.

It can furthermore be preferred if the catalyst support is formed as a shaped body, preferably as a sphere, cylinder, perforated cylinder, trilobe, ring, star or as a strand, preferably as a ribbed strand or a star strand, particularly preferably as a sphere.

It can further be preferred if the shaped body has a hardness greater than/equal to 20 N, preferably greater than/equal to 25 N, further preferably greater than/equal to 35 N and most preferably greater than/equal to 40 N.

In addition, it can be preferred if the catalyst support is formed as a sphere with a diameter greater than 2 mm, preferably with a diameter greater than 3 mm and preferably with a diameter greater than 4 mm.

The following embodiment example serves to explain the invention:

Example 1

500 g of an acid-treated dried powdery bentonite mixture based on a natural bentonite with montmorillonite as main constituent was ground into an intimate mixture by means of a ball mill with 2 to 50 g $Fe_2O_3$ and 10 g methyl cellulose customary in the trade.

The resultant mixtures were taken up with water and processed by means of a mixer into a dough from which spherical shaped bodies were produced under pressure by means of a tablet press. For hardening, the spheres were calcined at a temperature of 550° C. over a period of 7 h. From this shaped bodies were obtained which have the characteristics listed in Table 3:

TABLE 3

| Geometric form | Sphere |
| --- | --- |
| Diameter | 5 mm |
| Moisture content | <1.50 mass.-% |
| Compressive strength | >28 N |
| Bulk density | ca. 560 g l$^{-1}$ |
| Water absorbency | ca. 64% |
| Specific surface area (BET) | 125 m$^2$ g$^{-1}$ |
| SiO$_2$ content | 80 to 90 mass-% |
| Fe$_2$O$_3$ content | 0.5 to 9.5 mass-% |
| Other metal oxides | 2 to 10 mass-% |
| Loss on ignition 1000° C. | <0.4 mass-% |
| Acidity | 30-48 µval/g |
| BJH pore volume N$_2$ | 0.3-0.45 cm$^3$ g$^{-1}$ |

An Innojet Technologies (Lörrach, Germany) fluidized-bed device with the trade name Innojet® Aircoater was filled with 225 g of the spheres, produced as above, and the spheres were converted, by means of compressed air (6 bar) temperature-controlled at 80° C., into a fluidized-bed state in which the shaped bodies circulated toroidally, i.e. moved on a vertically aligned ellipsoid path and a horizontal circular path aligned perpendicular to this.

Once the shaped bodies were temperature-controlled at approx. 75° C., 300 ml of an aqueous noble-metal mixed solution containing 7.5 g Na$_2$PdCl$_4$ (sodium tetrachloropalladate) customary in the trade and 4.6 g NaAuCl$_4$ (sodium tetrachloroaurate) customary in the trade was sprayed onto the fluidized bed of the shaped bodies over a period of 40 min.

After the impregnation of the catalyst supports with the noble-metal mixed solution the support spheres were evenly sprayed with a 0.05 molar NaOH solution in the fluidized-bed state under the above conditions over a period of 30 min. The NaOH solution was allowed to act on the shaped bodies for 16 h.

Following exposure to the action of the NaOH, the supports were washed with plenty of water in the fluidized-bed device, in order to very largely remove from the support the alkali metal and chloride introduced into the support via the noble-metal compounds and NaOH.

After washing, the shaped bodies were dried in the fluidized-bed device by means of hot process air at a temperature of 100° C.

After the shaped bodies were dried they were reduced to a Pd/Au shell catalyst with a gas mixture of ethylene (5 vol.-%) in nitrogen at a temperature of approx. 150° C. in the fluidized-bed device.

The resulting shell catalyst contained approx. 1.2 mass-% Pd and had an Au/Pd atomic ratio of approx. 0.5, a shell thickness of approx. 160 µm and a hardness of 26 N.

The noble-metal concentration of the thus-produced Pd/Au shell catalyst varied over an area of 90% of the shell thickness, the area being at a distance of 5% of the shell thickness from each of the outer and inner shell limit, from the average noble-metal concentration of this area by a maximum of +/−10%.

The invention claimed is:

1. A shell catalyst, comprising an oxidic porous catalyst support, formed as a shaped body, with an outer shell in which metallic Pd and Au are contained, wherein the catalyst support is doped with at least one oxide of an element selected from the group consisting of Li, P, Ca, V, Cr, Mn, Fe, Sr, Nb, Ta, W, La and the rare-earth metals, and wherein the noble-metal concentration of the catalyst varies over an area of 90% of the shell thickness, the area being at a distance of 5% of the shell thickness from each of the outer and inner shell limit, from the average noble-metal concentration of this area by a maximum of +/−20%.

2. The catalyst according to claim 1, wherein the inner surface of the catalyst support is doped with the doping oxide.

3. The catalyst according to claim 1, wherein the dopant oxide is contained evenly distributed in the framework structure of the catalyst support.

4. The catalyst according to claim 1, wherein the catalyst support comprises a silicon oxide, aluminum oxide, aluminosilicate, zirconium oxide, titanium oxide, a natural sheet silicate, in particular an acid-treated calcined bentonite, or a mixture of two or more thereof.

5. The catalyst according to claim 1, wherein the doping oxide is contained in the catalyst support in a proportion of 0.01 to 25 mass-%, preferably in a proportion of 0.02 to 20 mass-% and preferably in a proportion of 0.05 to 20 mass-%, relative to the mass of the catalyst support.

6. The catalyst according to claim 1, wherein the catalyst support has an average pore diameter of 8 to 50 nm, preferably from 10 to 35 nm and preferably 11 to 30 nm.

7. The catalyst according to claim 1, wherein the catalyst support has an integral pore volume according to BJH of between 0.25 and 0.7 ml/g, preferably between 0.3 and 0.6 ml/g and preferably 0.35 to 0.5 ml/g.

8. The catalyst according to claim 1, wherein the catalyst support has an acidity of between 1 and 150 µval/g, preferably between 5 and 130 µval/g, preferably between 10 and 100 µval/g and particularly preferably between and 10 and 60 µval/g.

9. The catalyst according to claim 1, wherein the catalyst support has a surface area of less than/equal to 160 m$^2$/g, preferably less than 140 m$^2$/g, preferably less than 135 m$^2$/g, further preferably less than 120 m$^2$/g, more preferably less than 100 m$^2$/g, still more preferably less than 80 m$^2$/g and particularly preferably less than 65 m$^2$/g.

10. The catalyst according to claim 1, wherein the catalyst support has a surface area of 160 to 40 m$^2$/g, preferably between 140 and 50 m$^2$/g, preferably between 135 and 50 m$^2$/g, further preferably between 120 and 50 m$^2$/g, more preferably between 100 and 50 m$^2$/g and most preferably between 100 and 60 m$^2$/g.

11. The catalyst according to claim 1, wherein the catalyst has a hardness greater than/equal to 20 N, preferably greater than/equal to 25 N, further preferably greater than/equal to 35 N and most preferably greater than/equal to 40 N.

12. The catalyst according to claim 1, wherein the catalyst support comprises a natural sheet silicate, in particular an acid-treated calcined bentonite, preferably in a proportion of greater than/equal to 50 mass-%, preferably greater than/equal to 60 mass-%, preferably greater than/equal to 70 mass-%, further preferably greater than/equal to 80 mass-%, more preferably greater than/equal to 90 mass-% and most preferably greater than/equal to 95 mass-%, relative to the mass of the catalyst support.

13. The catalyst according to claim 12, wherein the sheet silicate contained in the catalyst support has an $SiO_2$ content of at least 65 mass-%, preferably at least 80 mass-% and preferably 95 to 99.5 mass-%.

14. The catalyst according to claim 12, wherein the natural sheet silicate contained in the catalyst support contains less than 10 mass-% $Al_2O_3$, preferably 0.1 to 3 mass-% and preferably 0.3 to 1.0 mass-%.

15. The catalyst according to claim 1, having an intergral pore volume wherein at least 80%, preferably at least 85% and preferably at least 90%, of the integral pore volume of the catalyst support is formed from mesopores and macropores.

16. The catalyst according to claim 1, wherein the catalyst support has a bulk density of more than 0.3 g/ml, preferably more than 0.35 g/ml and particularly preferably a bulk density of between 0.35 and 0.6 g/ml.

17. The catalyst according to claim 1, wherein the catalyst support is formed as a sphere, cylinder, perforated cylinder, trilobe, ring, cartwheel, "reverse" cartwheel, star or as a strand, preferably as a ribbed strand or star strand, preferably as a sphere.

18. The catalyst according to claim 17, wherein the catalyst support is formed as a sphere with a diameter of more than 2 mm, preferably a diameter of more than 3 mm and preferably a diameter of more than 4 mm.

19. The catalyst according to claim 1, wherein the shell of the catalyst has a thickness of less than 300 μm, preferably less than 200 μm, preferably less than 150 μm, further preferably less than 100 μm and more preferably less than 80 μm.

20. The catalyst according to claim 1, wherein the shell of the catalyst has a thickness of between 200 and 2000 μm, preferably between 250 and 1800 μm, preferably between 300 and 1500 μm and further preferably between 400 and 1200 μm.

21. The catalyst according to claim 1, wherein the proportion of Pd in the catalyst is 0.6 to 2.5 mass-%, preferably 0.7 to 2.3 mass-% and preferably 0.8 to 2 mass-%, relative to the mass of the catalyst support loaded with noble metal.

22. The catalyst according to claim 1, having an Au/Pd atomic ratio of the catalyst of between 0 and 1.2, preferably between 0.1 and 1, preferably between 0.3 and 0.9 and particularly preferably between 0.4 and 0.8.

23. The catalyst according to claim 1, wherein the noble-metal concentration of the catalyst varies over an area of 90% of the shell thickness, the area being at a distance of 5% of the shell thickness from each of the outer and inner shell limit, from the average noble-metal concentration of this area by a maximum of +/−15% and preferably by a maximum of +/−10%.

24. The catalyst according to claim 1, having a chloride content of less than 250 ppm, preferably less than 150 ppm.

25. The catalyst according to claim 1, comprising an alkali metal acetate, preferably potassium acetate.

26. The catalyst according to claim 25, wherein the alkali metal acetate content of the catalyst is 0.1 to 0.7 mol/l, preferably 0.3 to 0.5 mol/l.

27. The catalyst according to claim 25, having an alkali metal/Pd atomic ratio of between 1 and 12, preferably between 2 and 10 and preferably between 4 and 9.

28. A method of catalysis, comprising reacting one or more compounds with oxygen in an oxidation reaction in the presence of the catalyst of claim 1.

29. The method of claim 28, wherein the oxidation reaction comprises a synthesis of vinyl acetate monomer.

30. The method of claim 29, wherein the oxidation reaction comprises a gas-phase oxidation of ethylene and acetic acid to vinyl acetate monomer.

31. The method of claim 28, wherein the one or more compounds comprise one or more alkenyl compounds and one or more carboxyl compounds reacted to form one or more alkenylalkanoates.

32. A method of catalysis, comprising reacting one or more compounds with hydrogen in a hydrogenation reaction in the presence of the catalyst of claim 1.

33. A method of catalysis, comprising reacting one or more hydrogen-containing compounds in a dehydrogenation reaction in the presence of the catalyst of claim 1.

34. A method of catalysis, comprising reacting one or more sulphur-containing compounds with hydrogen in a hydrogenating desulphurization reaction in the presence of the catalyst of claim 1.

35. A method of catalysis, comprising reacting one or more oxygen-containing compounds in the presence of hydrogen in a hydrodeoxidation reaction in the presence of the catalyst of claim 1.

36. A method of catalysis, comprising reacting one or more nitrogen-containing compounds in the presence of hydrogen in a hydrodenitrification reaction in the presence of the catalyst of claim 1.

37. A method for producing a shell catalyst for producing vinyl acetate monomer (VAM), comprising the steps of
a) providing an oxidic porous catalyst support, formed as a shaped body, which is doped with at least one oxide of an element selected from the group consisting of Li, P, Ca, V, Cr, Mn, Fe, Sr, Nb, Ta, W, La and the rare-earth metals;
b) depositing a solution of a Pd precursor compound onto the catalyst support;
c) depositing a solution of an Au precursor compound onto the catalyst support;
d) converting the Pd component of the Pd precursor compound into the metal form and
converting the Au component of the Au precursor compound into the metal form, to form the shell catalyst, wherein the noble-metal concentration of the catalyst varies over an area of 90% of the shell thickness, the area being at a distance of 5% of the shell thickness from each of the outer and inner shell limit, from the average noble-metal concentration of this area by a maximum of +/−20%.

38. The method according to claim 37, wherein the Pd and Au precursor compounds are selected from the halides, oxides, nitrates, nitrites, formates, propionates, oxalates, acetates, hydroxides, hydrogen carbonates, amine complexes or organic complexes of these metals.

39. The method according to claim 37, wherein the Pd precursor compound is selected from the group consisting of $Pd(NH_3)_4(OH)_2$, $Pd(NH_3)_4(OAc)_2$, $H_2PdCl_4$, $Pd(NH_3)_4(HCO3)_2$, $Pd(NH_3)_4(HPO_4)$, $Pd(NH_3)_4Cl_2$, $Pd(NH_3)_4$ oxalate, $Pd(NO_3)_2$, $Pd(NH_3)_4(NO_3)_2$, $K_2Pd(OAc)_2(OH)_2$, $Pd(NH_3)_2(NO_2)_2$, $K_2Pd(NO_2)_4$, $Na_2Pd(NO_2)_4$, $Pd(OAc)_2$, $PdCl_2$ and $Na_2PdCl_4$.

40. The method according to claim 37, wherein the Au precursor compound is selected from the group consisting of $KAuO_2$, $HAuCl_4$, $KAu(NO_2)_4$, $AuCl_3$, $NaAuCl_4$, $KAu(OAc)_3(OH)$, $HAu(NO_3)_4$, $NaAuO_2$, $NMe_4AuO_2$, $RbAuO_2$, $CsAuO_2$, $NaAu(OAc)_2(OH)$, $RbAu(OAc)_2OH$, $CsAu(OAc)_2OH$, $NMe_4Au(OAc)_3OH$ and $Au(OAc)_3$.

41. The method according to claim 37, wherein the Pd and the Au precursor compound are deposited onto the catalyst support by steeping the catalyst support in the solution of the Pd precursor compound and in the solution of the Au precursor compound or in a solution which contains both the Pd and the Au precursor compound.

42. The method according to claim 37, wherein the solution of the Pd precursor compound and the solution of the Au precursor compound are deposited onto the catalyst support by spraying the solutions onto a fluid bed or a fluidized bed of the catalyst support, preferably by means of an aerosol of the solutions.

43. The method according to claim 37, wherein the catalyst support is heated during the deposition of the solutions.

44. The method according to claim 37, wherein
 a) a first solution of a Pd and/or an Au precursor compound is provided;
 b) a second solution of a Pd and/or an Au precursor compound is provided, wherein the first solution effects a precipitation of the noble-metal component(s) of the precursor compound(s) of the second solution and vice versa;
 c) the first and the second solution are deposited onto the catalyst support.

45. The method according to claim 44, wherein the precursor compounds of the first solution are acid and those of the second solution are basic.

46. The method according to claim 37, wherein the catalyst support is subjected to a fixing step, after the Pd and/or the Au precursor compound has/have been deposited onto the catalyst support.

47. A method for producing a shell catalyst for producing vinyl acetate monomer (VAM), comprising the steps of
 a) providing a powdery oxidic porous support material which is doped with at least one oxide of an element selected from the group consisting of Li, P, Ca, V, Cr, Mn, Fe, Sr, Nb, Ta, W, La and the rare-earth metals, wherein the support material is loaded with a Pd and an Au precursor compound or with Pd and Au particles;
 b) depositing the loaded support material onto a support structure in the form of a shell;
 c) calcining the loaded support structure from step b);
 d) optionally, converting the Pd and the Au component of the Pd or Au precursor compound into the metal form, wherein the noble-metal concentration of the catalyst varies over an area of 90% of the shell thickness, the area being at a distance of 5% of the shell thickness from each of the outer and inner shell limit, from the average noble-metal concentration of this area by a maximum of +/−20%.

* * * * *